June 27, 1944. W. E. LAMMERTS Plant Pat. 631
ROSE PLANT
Filed Dec. 15, 1943
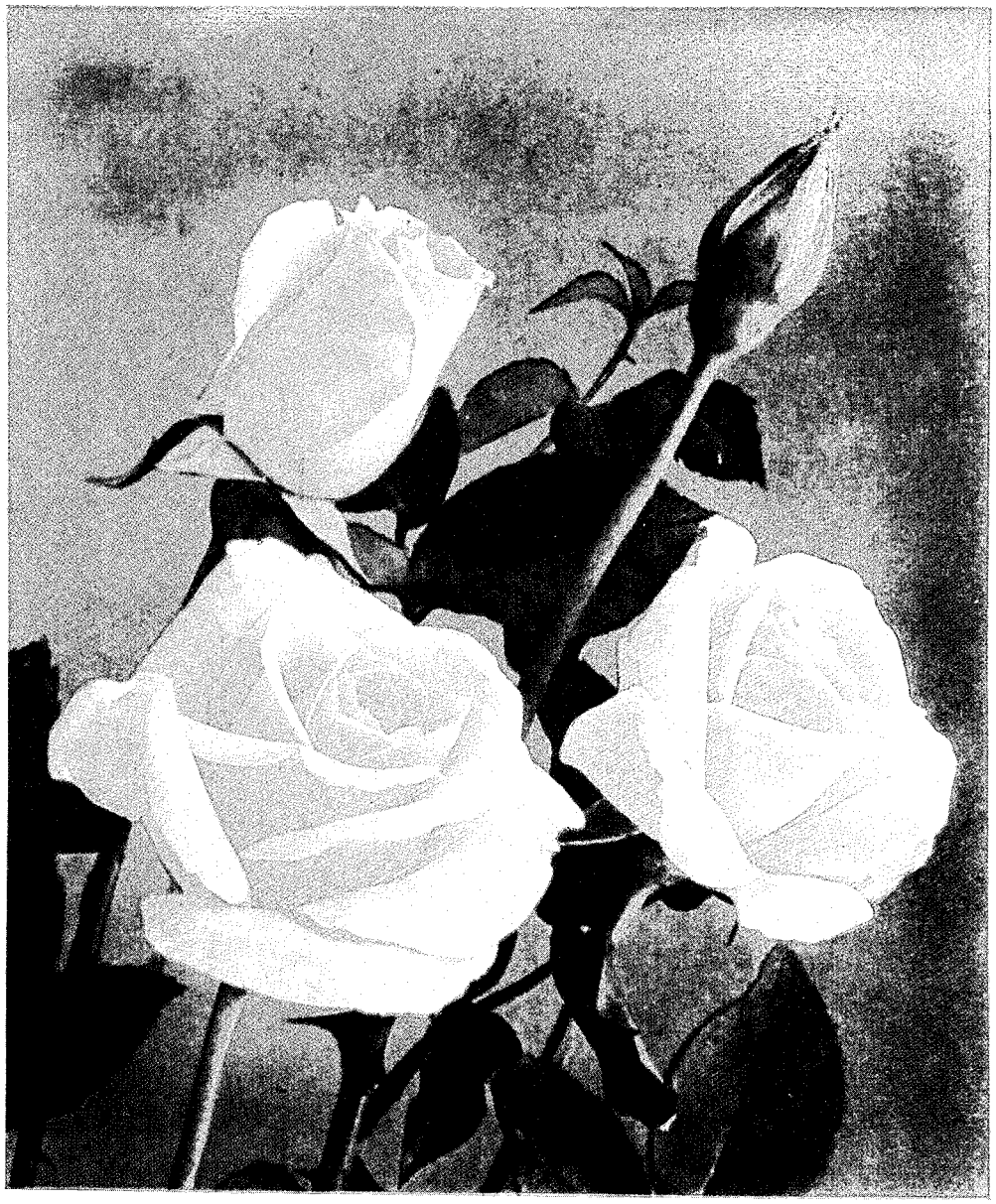
Inventor
W. E. Lammerts
By: Robbs & Robbs
Attorneys.

Patented June 27, 1944

UNITED STATES PATENT OFFICE

631

ROSE PLANT

Walter E. Lammerts, West Los Angeles, Calif., assignor to Armstrong Nurseries, Inc., Ontario, Calif., a corporation of California Application December 15, 1943, Serial No. 514,408

1 Claim. (Cl. 47—61)

The present invention relates to a new and distinct variety of Rose plant, a seedling from the cross of the well known varieties "Mrs. Sam McGredy" and "President Herbert Hoover."

Both of the last-named roses have been universally very satisfactory, but the present progeny thereof shows marked improvements thereover, particularly in reference to its intense, sweet fragrance, the beauty of its long-pointed buds and highly centered newly opened flower, these outstanding characteristics adapting it more especially for corsage use.

Comparing the new rose to its parents, it may be noted that in habit of growth and bud form, it is similar to "President Herbert Hoover" but with somewhat bushier habit, the fragrance of its flowers more nearly approaching that of "President Hoover," but sweeter and more intense. The coloring of the flowers, as will be observed from the accompanying illustration, appears to be intermediate that of its parents, though again more nearly resembling "President Hoover" in this respect in bud but opening to a Pink Rose with Yellow base as distinguished from the Creamy Yellow of the opening stage of "President Hoover." The form of the open bloom of this new rose is somewhat between that of its parents while its foliage and thorns come closer to those of its parent "Mrs. Sam McGredy," as does also the quantity of flower.

The characteristic of having usually only one flower to a stem is more nearly like that of "President Hoover." It differs from these parents further in having more resistance to mildew than "President Hoover" and more resistance to blackspot than "Mrs. Sam McGredy."

It is at its best in the cool coastal climate, but is excellent in the hotter interior regions during the spring and fall blooming seasons.

A sexual reproduction of this new variety shows the foregoing characteristics come true to form and are established.

The following is a detailed description of this new rose, the color terminology employed herein being in accord with that of the Robert F. Wilson Horticultural Colour Chart, except where obviously the meaning is the sense of the popular color term.

Type: Half hardy; bush; outdoor; seedling; for cut flowers and garden decoration.

Class: Hybrid tea.

Breeding or discovery: Seedling.

*Seed parent.*—"Mrs. Sam McGredy."

*Pollen parent.*—"President Herbert Hoover."

Propagation: Holds its distinguishing characteristics through succeeding propagations by budding which is the only method tried up to the present.

*Flower*

Locality where grown: Ontario, California.

Flowers borne: Singly, two, three or several to stem; in irregular, flat cluster; on strong, medium length stems.

Quantity of bloom: Abundant; outdoors.

Continuity: Nearly continuous in Southern California.

Fragrance: Moderate to strong; tea.

Bud:

*Pedicel.*—Medium length; slender; erect; smooth; numerous gland-tipped cilia; no hairs. *Color*—Fern Green—o862/1—Chart II, page 186.

*Before calyx breaks.*—*Size*—medium. *Form*—pointed, without foliaceous appendages on the surface of the bud; with slender, much-cut foliaceous parts extending beyond the tip of the bud equal to three-fourths or more of its length.

*As calyx breaks.*—*Color*—Cherry—722—Chart II, page 157, to Currant-Red—821/3—Chart II, page 167. *Inner surface*—with woolly tomentum; alternate margins; lined with gland-tipped cilia or stipitate hairs.

*As first petal opens.*—*Size*—medium. *Form*—globular. *Color*—outside—Porcelain Rose—620/1—Chart II, page 147, to Carmine Rose—621/1—Chart I, page 75. Inside—Dawn Pink—523—Chart II, page 137, to Delft Rose—o20/2—Chart II, page 108. *Opening*—opens up well. Is retarded by cold.

Bloom:

*Size.*—When fully open—medium; four inches to five inches.

*Petalage.*—Semi-double; from 23 to 25 petals; arranged regularly.

*Form.*—High center at first; becoming open; petals remaining at first very loose; becoming later, at maturity, very loosely cupped.

Petals: Soft; with inside satiny and outside velvety.

*Shape.*—Outside—round; apex formed with two notches. Intermediate—round; apex formed with one notch. Inside—mucronate; apex formed with one notch.

*Color.*—Modified by being shaded at margin with Empire Rose—o621/1—Chart II, page 183, and fading to Spinel Pink—o625/1—Chart II, page 184, as petals become older or as the Yellow radiating from the base fades out. Also, shaded at base with Mimosa-Yellow—6o2—Chart II, page 143, and fading to Mimosa-Yellow—6o2/2—Chart II, page 143.

This description of a newly opened flower was made from a rose grown outdoors, in October, 1942, at Ontario, California:

*Color.*—Outside petal: Outside surface—Spinel Pink—o625/1—Chart II, page 184, to Empire Rose—o621/1—Chart II, page 183. Inside surface—Carmine Rose—621/1—Chart I, page 75. Intermediate petal: Outside surface—Porcelain Rose—620/2—Chart I, page 147. Inside surface—Empire Rose—o621/1—Chart II, page 183. Inner petal: Outside surface—Empire Rose—o621/1—Chart II, page 183. Inside surface—Coral Pink—o619/1—Chart II, page 182. Outside, intermediate, and inner petals shaded at base with Mimosa Yellow—6o2—Chart II, page 143, and radiating outward to a Naples Yellow—403—Chart II, page 121.

This description was made from a rose that was open for three days outdoors, in October, 1942, at Ontario, California:

*Color.*—Outside petal: outside surface—Neyron Rose—623/2—Chart I, page 76. Inside surface—Carmine Rose—621/2—Chart I, page 75. Inside petal: Outside surface—Dawn Pink—523/1—Chart II, page 137. Inside surface—Venetian Pink—420—Chart II, page 125. Outside and inside petals shaded at tip of base with Mimosa Yellow—6o2—Chart II, page 143, and radiating outward to a Naples Yellow—403—Chart II, page 121.

*General color effect.*—Newly opened flower—Dawn Pink—523/1—Chart II, page 137. Three days open—Spinel Pink—o625/1—Chart II, page 184.

*Behavior.*—Drop off cleanly; affected by dry weather. Opens up quickly in hot weather, appearing shaggy when open. Fades to a Rhodamine Pink—527/1—Chart II, page 138, and Naples Yellow—4o3/3—Chart II, page 121.

*Flower longevity.*—On bush in garden four days in October; cut roses grown outdoors kept at living-room temperatures five days in October.

*Reproductive organs*

Stamens: Many; arranged regularly about pistils, mixed with petaloids and tucked in calyx.

Filaments: Medium length; Yellow—o7/1—Chart II, page 101. Base, Mars Orange—o13—Chart II, page 104. Most with anthers.

Anthers: Medium size; all open at once.
*Color.*—Chrome Yellow—605/1—Chart II, page 144.

Pollen: Moderate in amount.
*Color.*—Majolica-Yellow—o9—Chart II, page 102.

Pistils: Many. Tip, Currant Red—821—Chart II, page 167. Base, Sap Green—62/1—Chart II, page 62.

Styles: Even; medium length; medium heavy; bunched.

Stigma: Amber Yellow—5o5/2—Chart II, page 132.

Ovaries: All enclosed in calyx.

Hips: Very globular, with conspicuous neck; pear-shaped.
*Color.*—Fern Green—o862—Chart II, page 186. Very smooth; walls thick, fleshy.

Sepals: Permanent; very long; spear-shaped.
*Color.*—Lettuce Green—861—Chart II, page 176, inside. Fern Green—o862—Chart II, page 186, outside.

Seeds: Few; medium size.

Foliage:
*Leaves.*—Compound of five to seven leaflets; normal in amount; medium size; leathery; semi-glossy.
*Leaflets.*—Shape—oval, with apex mucronate; base, obtuse. Margin, irregularly dentate to serrate.
*Color.*—*Mature*—upper surface—Parsley Green—oo962—Chart II, page 193. Under surface—Spinach Green—o960/3—Chart II, page 187. *Young*—upper surface—margin, Garnet-Brown—oo918—Chart II, page 192, to Fern Green—o862/3—Chart II, page 186. Under surface—Garnet-Brown—oo918—Chart II, page 192.
*Rachis.*—Heavy. Upper side—grooved; glandular. Under side—moderately hairy.
*Stipules.*—Glandular; long; moderately wide; with moderately long points, turning out at an angle of less than 45°, slightly recurved toward the stem.
*Disease.*—Resistant to mildew.

Growth:
*Habit.*—Bushy; upright; much branched.
*Growth.*—Free to vigorous.
*Canes.*—Medium heavy.
*Main stems.*—*Color*—Spinach Green—o960/3—Chart II, page 187, with cracks in bark forming corky linear dots and lines along the stem. *Large prickles*—many; long; pointed slightly down to straight; with short, oval base. Color—Garnet Brown—oo918/3—Chart II, page 192, *Small prickles*—many. Color—Garnet Brown—oo918/3—Chart II, page 192. *Hairs*—several. Color—Garnet Brown—oo918/3—Chart II, page 192.
*Branches.*—*Color*—Spinach Green—o960/3—Chart II, page 187, with cracks in bark forming corky linear dots and lines along the stem. *Large prickles*—many; long to slightly straight downward; with short, oval base. Color—Garnet Brown—oo918/3—Chart II, page 192. *Small prickles*—few. Color—Garnet Brown—oo918/3—Chart II, page 192. *Hairs*—few. Color—Garnet Brown—oo918/3—Chart II, page 192.
*New shoots.*—*Color*—Fern Green—o862—Chart II, page 186. *Large prickles*—several; long; straight to slightly down; with narrow, oval base. Color—Garnet Brown—oo918/3—Chart II, page 192. Tip, Fern Green—o862—Chart II, page 186. *Small prickles*—few, in groups and singularly. Color—Garnet Brown—oo918/3—Chart II, page 192. *Hairs*—few; glandular in groups and singularly. Color—Garnet Brown—oo918/3—Chart II, page 192.

I claim:

A new and distinct variety of Rose plant characterized as to novelty by its habit of bushy growth, disease resistance, the beauty of its long pointed buds and high centered newly opened flowers, and the color and intense sweet fragrance of these flowers, substantially as shown and described.

WALTER E. LAMMERTS.